United States Patent
Haissaguerre

(10) Patent No.: US 7,047,068 B2
(45) Date of Patent: May 16, 2006

(54) MICROELECTRODE CATHETER FOR MAPPING AND ABLATION

(75) Inventor: Michel Haissaguerre, Durand (FR)

(73) Assignee: C.R. Bard, Inc., Murray Hill, NJ (US)

( * ) Notice: Subject to any disclaimer, the term of this patent is extended or adjusted under 35 U.S.C. 154(b) by 122 days.

(21) Appl. No.: 10/450,275

(22) PCT Filed: Dec. 11, 2001

(86) PCT No.: PCT/US01/47888

§ 371 (c)(1),
(2), (4) Date: Dec. 12, 2003

(87) PCT Pub. No.: WO02/056783

PCT Pub. Date: Jul. 25, 2002

(65) Prior Publication Data
US 2004/0082860 A1    Apr. 29, 2004

Related U.S. Application Data

(60) Provisional application No. 60/254,630, filed on Dec. 11, 2000.

(51) Int. Cl.
A61B 5/05 (2006.01)

(52) U.S. Cl. .................... 600/547; 600/466

(58) Field of Classification Search ............ 600/466, 600/547

See application file for complete search history.

(56) References Cited

U.S. PATENT DOCUMENTS

| | | | |
|---|---|---|---|
| 5,366,443 A | 11/1994 | Eggers et al. | |
| 5,688,266 A | 11/1997 | Edwards et al. | |
| 5,797,960 A * | 8/1998 | Stevens et al. | 606/213 |
| 5,842,998 A * | 12/1998 | Gopakumaran et al. | 600/547 |
| 5,871,469 A | 2/1999 | Eggers et al. | |
| 5,916,158 A | 6/1999 | Webster, Jr. | |
| 5,916,213 A * | 6/1999 | Haissaguerre et al. | 606/41 |

FOREIGN PATENT DOCUMENTS

| | | |
|---|---|---|
| EP | 0 629 382 A1 | 12/1994 |
| EP | 0 797 956 A2 | 10/1997 |
| EP | 0 965 302 A | 12/1999 |
| WO | WO 99 00060 A | 1/1999 |

\* cited by examiner

Primary Examiner—George Manuel
(74) Attorney, Agent, or Firm—Wolf, Greenfield & Sacks, P.C.

(57) ABSTRACT

Catheter for mapping and/or ablation, and methods of using the same. According to one embodiment, catheter includes a metallic cap having a plurality of apertures and at least one electrode disposed in each aperture of the plurality of apertures. According to another embodiment, the catheter includes a non-conductive cap having a plurality of apertures and at least one electrode disposed in each aperture of the plurality of apertures. Electrodes may be paired, arranged along the length of the cap, or circumferentially arranged on the cap, according to various embodiments. According to a further embodiment, a method for treating a condition of a heart includes placing a catheter inside the heart, mapping a region of the heart using mapping electrodes on the catheter, and ablating using an ablation electrode disposed about the mapping electrodes of the catheter.

1 Claim, 5 Drawing Sheets

MICROELECTRODE CATHETER FOR MAPPING AND ABLATION

CROSS REFERENCE TO RELATED APPLICATIONS

This application claims the benefit of U.S. provisional application Ser. No. 60/254,630 entitled "Microelectrode Catheter for Mapping, Ablation, and Localization," filed Dec. 11, 2000, which is hereby incorporated herein by reference.

BACKGROUND OF THE INVENTION

1. Field of the Invention

The invention relates to medical devices for performing mapping and ablation procedures. More particularly, the invention relates to methods and apparatus for performing mapping and ablation procedures using a single catheter.

2. Discussion of the Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

SUMMARY OF THE INVENTION

The present invention encompasses apparatus and methods for mapping electrical activity within the heart. The present invention also encompasses methods and apparatus for creating lesions in the heart tissue (ablating) to create a region of necrotic tissue which serves to disable the propagation of errant electrical impulses caused by an arrhythmia.

In one embodiment, the present invention includes a catheter comprising a metallic cap including a plurality of apertures and at least one electrode disposed in each aperture of the plurality of apertures.

According to another embodiment of the invention, the electrodes are insulated from the cap.

According to another embodiment of the invention, the electrodes extend beyond a surface of the cap.

According to another embodiment of the invention, the electrodes are mushroom-shaped.

According to another embodiment of the invention, the electrodes are dome-shaped.

According to another embodiment of the invention, the cap is gold.

According to another embodiment of the invention, the cap is platinum.

According to another embodiment of the invention, the catheter further comprises means for steering a distal end of the catheter.

According to another embodiment of the invention, the means for steering includes means for steering a distal end of the catheter in at least one plane.

According to another embodiment of the invention, the metallic cap may be used to perform ablation and the at least one electrode disposed in each aperture may be used to perform mapping.

According to another embodiment of the invention, the metallic cap is constructed and arranged to optimize ablation procedures and wherein a configuration of electrodes is selected to optimize mapping procedures.

According to another embodiment of the invention, a surface area of the metallic cap is larger than a surface area of the at least one electrode.

According to another embodiment of the invention, the catheter further comprises a localization sensor for identifying a location of the catheter.

According to another embodiment of the invention, the catheter further comprises a temperature sensor for sensing temperature in a vicinity of the catheter.

According to another embodiment of the invention, the catheter further comprises a temperature sensor for sensing temperature in a vicinity of the cap.

According to another embodiment of the invention, the catheter comprises means for irrigating in a vicinity of the catheter.

According to another embodiment of the invention, the catheter comprises means for irrigating in a vicinity of the cap.

In another embodiment, the invention includes a catheter further comprising a substantially cylindrical cap portion; a substantially dome-shaped cap portion disposed distal to the substantially cylindrical cap portion and first and second electrodes mounted to the substantially dome-shaped cap portion, but not to the substantially cylindrical cap portion.

According to another embodiment of the invention, the catheter further comprises a reference electrode mounted to the cylindrical cap portion.

According to another embodiment of the invention, the catheter has an axis that extends longitudinally along a length of the catheter and further includes at least one group of electrodes mounted to the cylindrical cap portion in a plane normal to the axis.

According to another embodiment of the invention, a plurality of electrodes mounted along a line that is parallel to the axis.

In another embodiment, the invention includes a method for treating a condition of a heart, comprising acts of placing a catheter inside the heart, mapping a region of the heart, using mapping electrodes on the catheter, and ablating, using an ablation electrode disposed about the mapping electrodes of the catheter.

In another embodiment, the invention includes a method of creating a lesion in heart tissue and determining a continuity of the lesion, comprising acts of providing a catheter having at least one ablation electrode and a plurality of mapping electrodes, placing the plurality of electrodes in contact with the heart tissue at the location of the lesion, creating a lesion in the heart tissue using the at least one ablation electrode, detecting a signal from each of the plurality of electrodes, determining, based on the signal from each of the plurality of electrodes, whether a signal exists between any adjacent electrodes, and assessing the continuity of the lesion.

In another embodiment, the invention includes a method of determining a location for a septal wall puncture, comprising acts of providing a catheter with first and second electrodes on a distal tip of the catheter, detecting a signal from each of the first and second electrodes, and determining, based on the signal from each of the first and second electrodes, an area of lowest conductivity on the septal wall.

BRIEF DESCRIPTION OF THE DRAWINGS

In the drawings, which are incorporated herein by reference and in which like elements have been given like reference characters.

DETAILED DESCRIPTION

In this description, various aspects and features of the present invention will be described. One skilled in the art will appreciate that the features may be selectively combined in a device depending on the particular application. Furthermore, any of the various features may be incorporated in a catheter and associated method of use for mapping and/or ablation procedures.

Catheter Overview

Figure 1:
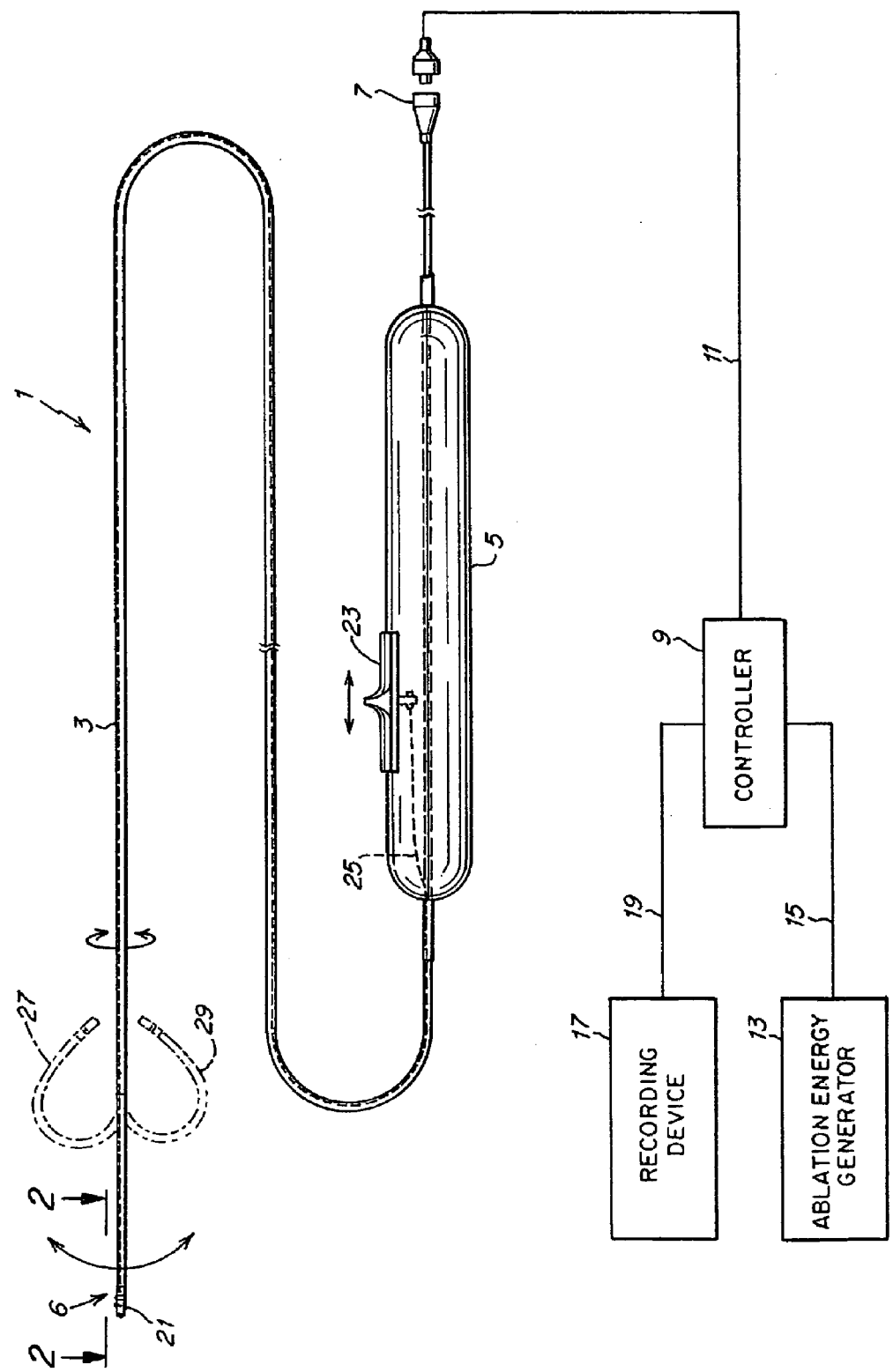
FIG. 1 illustrates an overview of a mapping and ablation catheter system in accordance with the present invention.

Reference is now made to FIG. 1, which illustrates an overview of a mapping and ablation catheter system for use in electrophysiology procedures, in accordance with the present invention. The system includes a catheter 1 having a shaft portion 3, a control handle 5, and a connector portion 7. When used in mapping applications, connector portion 7 is used to allow signal wires running from mapping electrodes at the distal end 6 of the catheter to be connected to a device for recording signals, such as a recording device 17. When used in ablation applications, connector portion 7 is used to allow signal wires running from ablation electrodes at the distal end 6 of the catheter to be connected to a device for generating ablation energy, such as ablation energy generator 13.

A controller 9 is electrically connected to connector portion 7 via cable 11. In one embodiment, controller 9 may be a QUADRAPULSE RF CONTROLLER™ device available from C. R. Bard, Inc., Murray Hill, N.J. Ablation energy generator 13 may be connected to controller 9 via cable 15. Recording device 17 may be connected to controller 9 via cable 19. When used in an ablation application, controller 9 is used to control ablation energy, provided by ablation energy generator 13, to catheter 1. When used in a mapping application, controller 9 is used to process signals from catheter 1 and provide these signals to recording device 17. Although illustrated as separate devices, recording device 17, ablation energy generator 13, and controller 9 may be incorporated into a single device. It should further be appreciated that although both ablation energy generator 13 and recording device 17 are illustrated in FIG. 1, either or both of these devices may be incorporated in the catheter system in accordance with the present invention.

The shaft portion 3 of the catheter 1 is, in one embodiment, approximately seven French in diameter, although it should be appreciated that many diameters are possible, and the diameter of shaft portion 3 may be smaller or larger depending on the particular application and/or combination of features incorporated into the catheter. Shaft portion 3 includes a distal cap portion 21 having a plurality of, for example, two or more electrodes. As will be subsequently described, the electrodes may be arranged in a number of different configurations and may include mapping and/or ablation electrodes. According to one embodiment of the invention, distal cap portion 21 is approximately eight mm in length.

Distal Cap Portion

Figure 2:
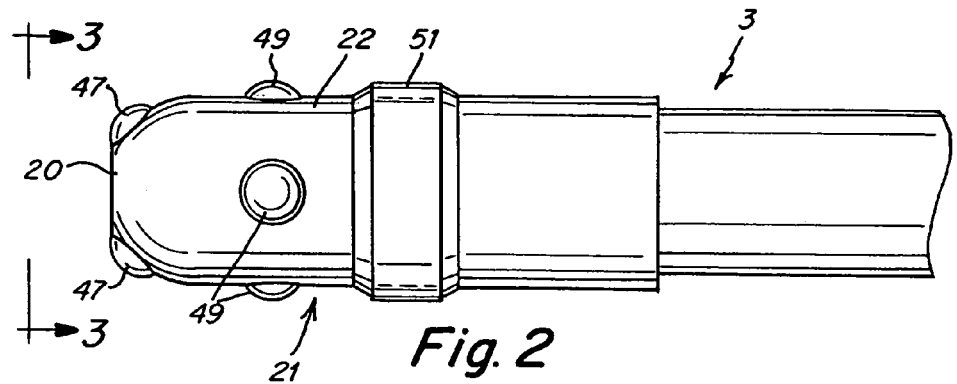
FIG. 2 illustrates a side view of the distal cap portion of the catheter of FIG. 1 in accordance with one embodiment of the present invention.
Figure 3:
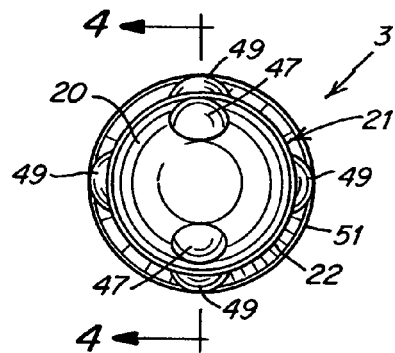
FIG. 3 illustrates an end view of the distal cap portion of the catheter of FIG. 2.

Reference is now made to FIGS. 2 and 3, which respectively illustrate a side elevation view of the distal cap portion 21 of catheter 1 along line B—B of FIG. 1, and an end elevation view of the distal cap portion 21 of catheter 1 along line D—D of FIG. 2. Distal cap portion 21 is provided, in the illustrated embodiment, with a first set of mapping electrodes 47, a second set of mapping electrodes 49, and a band electrode 51. The electrodes may be formed of any suitable bio-compatible, electrically conductive material (e.g., platinum, gold, titanium, iridium, stainless steel). The mapping electrodes 47, 49 are approximately 0.5–1.5 mm in diameter, though they may be either larger or smaller according to the invention. The size of mapping electrodes 47, 49 is in part determined based on considerations of signal quality, which improves as electrode size increases and as electrode isolation (i.e., distance between electrodes) increases.

The electrodes may have any of numerous shapes. In FIG. 2, mapping electrodes 47, 49 are shown having a circular shape. However, mapping electrodes 47, 49 may alternatively be square, oval, hexagonal, octagonal, or any other shape that may be readily imagined by one skilled in the art. Further, though mapping electrodes 47, 49 are also shown in FIG. 2, as well as FIGS. 3–5 and 7–12, as dome-shaped, the mapping electrodes of any of the illustrated embodiments may alternatively be flat so that they are more-closely flush with the surface of the distal cap portion 21, as shown, for example, by mapping electrodes 48, 50 in FIG. 6. Band electrode 51 is shown in FIG. 2 as flat, but may alternatively have a curved surface.

Figure 4:
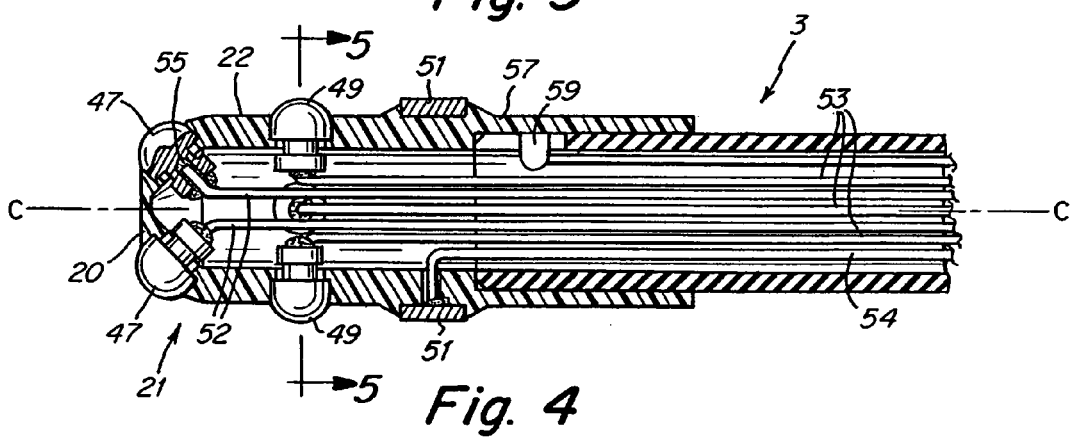
FIG. 4 illustrates a cross-sectional side view of the of the distal cap portion of the catheter of FIG. 2.
Figure 5:
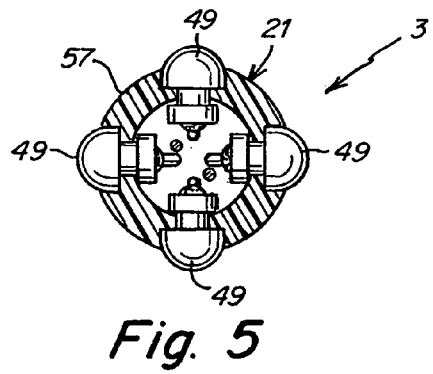
FIG. 5 illustrates a cross-sectional end view of the distal cap portion of the catheter of FIG. 2.

Reference is now made to FIGS. 4 and 5, which respectively illustrate a cross-sectional side view of the distal cap portion 21 of catheter 1 along line E—E of FIG. 3, and a cross-sectional axial view of the distal cap portion 21 of catheter 1 along line F—F of FIG. 4. As shown, wires 52, 53, 54 respectively connect to each of the electrodes 47, 49, 51 of the catheter 1. These wires 52, 53, 54, which maybe between 3/1000 mm and 20/1000 mm, allow electrical signal information to be transmitted from mapping electrodes 47, 49 and band electrode 51, when used in a mapping application, to connector portion 7, which in turn connects to controller 9 (FIG. 1). When electrode 51 is used in an ablation application, the wire 54 connected thereto may be used to transmit ablation energy from ablation energy generator 13 to the electrode via connector portion 7. The wires 52, 53, 54 are connected to the electrodes by soldering, welding, or any other suitable mechanism for connecting the wires to the electrodes to form an electrical connection. Mapping electrodes 47, 49 may be substantially mushroom-shaped, and may have a substantially cylindrical "stem" portion 48. As shown in FIGS. 4 and 5, the cylindrical stem 48 of each electrode 47, 49 may have a larger diameter at the base 46 of the stem, so that the electrode is prevented from dislodging from the distal cap portion 21. Distal cap portion 21 may also be countersunk at the location of each electrode, so that the electrodes are disposed within a recessed portion of the distal cap portion 21.

Mapping electrodes 47, 49 and band electrode 51 are disposed in apertures within a distal cap 57, which covers the distal cap portion 21 of the catheter 1. The distal cap 57 may be, in one embodiment, formed of any non-electrically conductive, bio-compatible material. For example, distal cap 57 may be formed of polyamide, epoxy, plastic, nylon, or any other suitable material. In addition to providing a durable surface, distal cap 57 isolates each of the electrodes on distal cap portion 21 from each other.

According to one aspect of the invention, the distal cap portion 21 is provided with a pair of mapping electrodes 47 at the distal end of catheter 1. The pair of mapping electrodes 47, in accordance with one embodiment of the invention, are disposed on the dome-shaped portion 20 of the distal cap 57, but not on the cylindrically-shaped portion 22 of the distal cap 57. Further, the mapping electrodes 47 may be positioned, in one embodiment, at a 45° angle with respect to an axis C—C that extends longitudinally along the length of catheter 1, through its center. The mapping electrodes 47 may be separated by a distance of approximately 1 mm. One skilled in the art will appreciate that other angles and separation distances for mapping electrodes 47 may be provided.

The pair of mapping electrodes 47 may be used to determine, for example, a location of lowest conductivity on the septal wall, or a preferred location to puncture the septal wall during a transeptal procedure. Each of the mapping electrodes 47 may detect a voltage signal, which is transmitted to controller 9 via wires 53. Voltage may be measured instantaneously or continuously by each of the electrodes 47. Continuous voltage measurements generate an electrogram (a voltage signal that changes with time) for each electrode 47. The voltage detected by each electrode 47 may be determined with respect to a reference electrode, termed a unipolar voltage measurement, or may be determined with respect to the other electrode 47 of the pair, termed a bipolar voltage measurement. Thus, the pair of mapping electrodes 47 may generate two unipolar electrograms, each with respect to a reference electrode located elsewhere on the catheter 1, or a single bipolar electrogram representing the voltage between each of the electrodes 47 of the pair.

In the bipolar mode, the use of two electrodes 47 enables the voltage between the electrodes to be determined. In the unipolar arrangement, the use of two electrodes enables an additional data point for locating the preferred site of puncture. For example, if a first electrode of the pair detects a lower amplitude signal than the second electrode of the pair, this information can be used to indicate that the distal cap portion 21 of catheter 1 should be moved in the direction of the first electrode, towards the lower amplitude signal. It should be appreciated that while the electrodes 47 are described as a pair of electrodes, a single electrode or more than two electrodes may alternately be used on the distal cap portion 21 in accordance with the invention.

A point of reduced conductivity is represented by a reduced or minimized voltage signal from one or more of the electrodes 47. This point may be detected by a computer algorithm and/or a human operator. For example, the controller 9 may implement an algorithm that integrates the continuous voltage signal over a period of time and compares the resultant value with a predetermined value or with other calculated values to determine whether the voltage signal is sufficiently low so as to indicate a point of lowest conductivity or a preferred site of puncture.

We have found that electrodes approximately one mm in size, spaced approximately one mm apart and set at approximately 45° with respect to axis c—c advantageously allows for accurate determination of the foramen ovale during transeptal procedures.

According to another aspect of the invention, the distal cap portion 21 is provided with a group of mapping electrodes 49 circumferentially disposed about the distal cap portion 21 of catheter 1. Reference is now made to FIGS. 2 through 12, which respectively illustrate side and perspective views of the distal cap portion 21 according to this aspect of the invention. The group of mapping electrodes 49 are disposed on the cylindrically-shaped portion 22 of the distal cap portion 21 in a plane (e.g. F—F) normal to the axis C—C (FIG. 4). The mapping electrodes 49 may be equidistant from each other and may be separated by a distance of at least half of the diameter of each electrode. In one embodiment, the group of mapping electrodes 49 includes four electrodes, though other numbers of electrodes (e.g., two, three, five, six) are also possible according to the invention.

Figure 10:
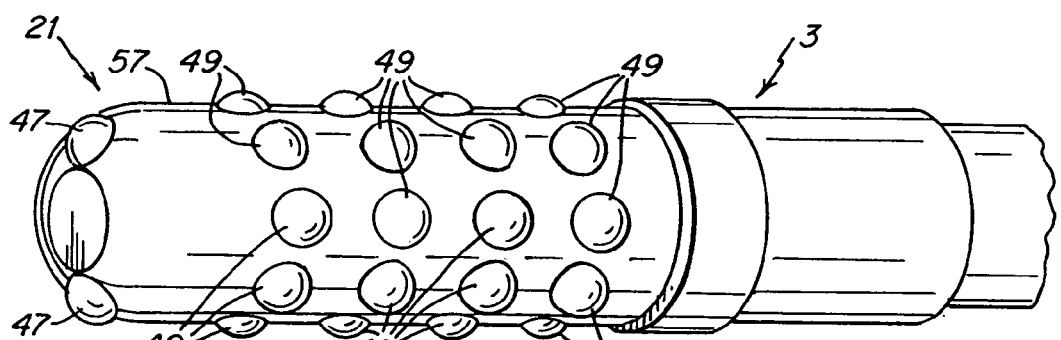
FIG. 10 illustrates a perspective view of the distal cap portion of a catheter in accordance with another embodiment of the present invention.

According to another aspect of the invention, the distal cap portion 21 is provided with a plurality of groups of mapping electrodes 49 circumferentially disposed about the distal cap portion 21 of catheter 1. As illustrated in FIG. 10, catheter 1 may be provided with four groups of mapping electrodes 49, which may, for example, comprise four electrodes each. The spacing of groups of electrodes 49 is, in one embodiment, approximately two millimeters.

One or more groups of mapping electrodes 49 may be used to determine the intensity, direction, and velocity of electrical signals of the heart. The group configuration of mapping electrodes 49 provides advantages over certain electrodes, e.g., band electrodes, which do not allow the same degree of differentiation between signals. For example, a band electrode cannot differentiate signals received from a various regions of the circumference of the catheter. In contrast, a group of four electrodes allows differentiation between signals from each quadrant of the circumference of the catheter, and therefore provides more directional information than a band electrode. Multiple groups of mapping electrodes 49 allows a greater degree of differentiation between signals received at various points along the length of a catheter. Further, because the signals received by different electrodes may be compared, the propagation of a signal along the length of the catheter may be tracked, and intensity, direction, and velocity of the propagating electrical signals may be calculated. Groups of mapping electrodes also allows for differentiation between signals of local and remote origin, based on a comparison of signals received by adjacent electrodes. For example, if a signal is measured more weakly by each successive adjacent electrode, and received after a constant time lapse by each successive electrode, one may determine that the signal is of remote origin (i.e., a "far-field" signal). In contrast, if a signal is received more strongly by a particular electrode than adjacent electrodes, and is not received earlier by an adjacent electrode, one may determine that the signal is of local origin (i.e., a "near-field" signal). Thus the configuration of mapping electrode 49 can provide a high resolution mapping catheter.

Figure 11:
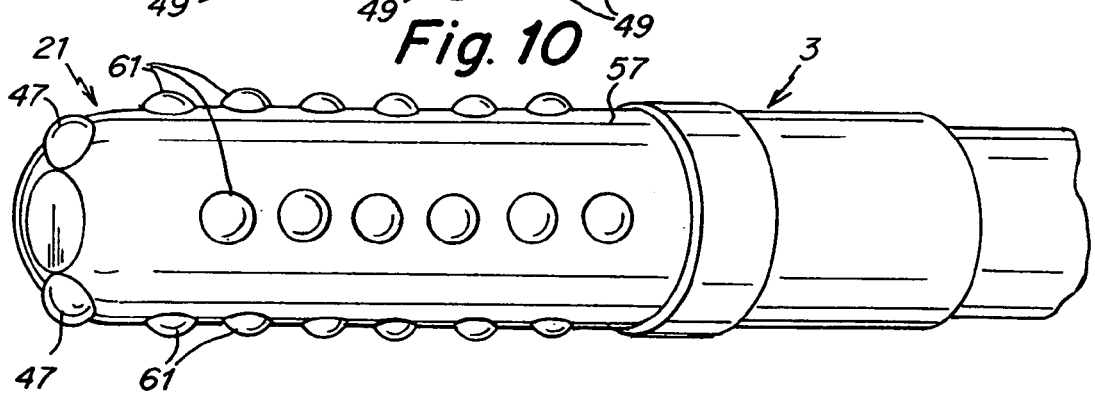
FIG. 11 illustrates a perspective view of the distal cap portion of a catheter in accordance with another embodiment of the present invention.

According to another aspect of the invention, the distal cap portion 21 is provided with a row of mapping electrodes 61 disposed along the length of distal cap portion 21. As illustrated in FIG. 11, each electrode 61 may be equidistant from each adjacent electrode disposed along the length of the catheter 1. The electrodes 61 may be similar to the electrodes of other embodiments, and may be approximately between 0.5 and 1.5 mm in diameter. In one embodiment, the catheter is provided with four mapping electrodes 61 disposed on the circumference of distal cap portion 21, although more or fewer mapping electrodes 61 may be used. The spacing of the electrodes 61 is, in one embodiment, approximately one mm.

The rows of mapping electrodes 61 that extend along the length of distal cap portion 21 may be used to determine the continuity of a line of lesions, e.g., formed by the "drag and burn" ablation technique. A voltage signal may be measured between each of the adjacent mapping electrodes 61 in a row of electrodes. The controller 9 may process each voltage signal and, for example, determine whether the voltage level for each signal exceeds a certain threshold, indicating that a gap in the lesions may exist. More generally, the row of mapping electrodes 61 may be used to determine the conductivity of the heart tissue in contact with the electrodes for any portion of heart tissue between any adjacent or non-adjacent pair of electrodes 61.

Figure 6:
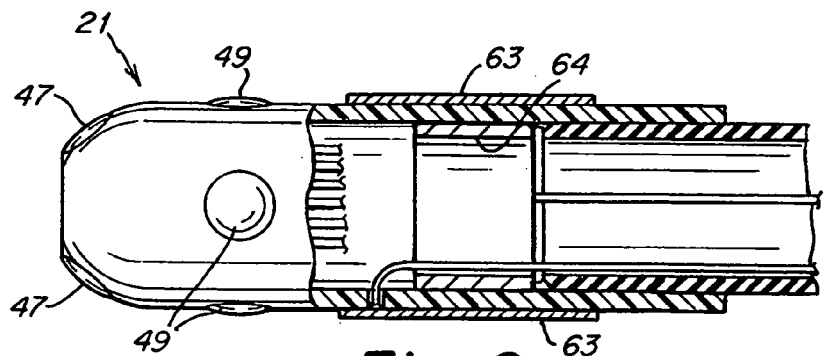
FIG. 6 illustrates a partial cross-sectional side view of the distal cap portion of a catheter in accordance with another embodiment of the present invention.
Figure 7:
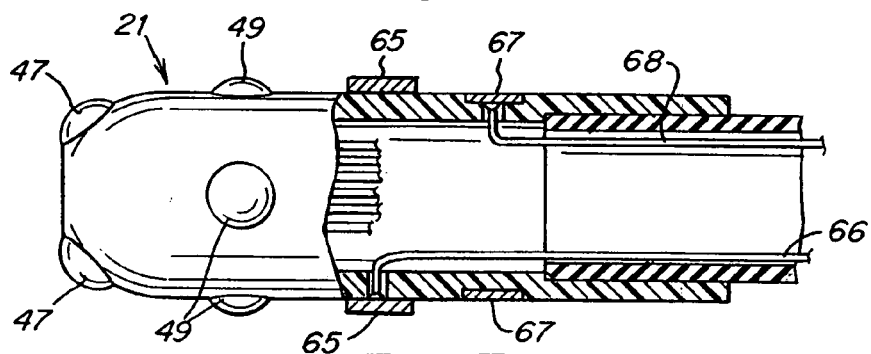
FIG. 7 illustrates a partial cross-sectional side view of the distal cap portion of a catheter in accordance with a another embodiment of the present invention.

According to another aspect of the invention, the distal cap portion 21 is provided with a band-shaped electrode disposed on the distal cap 57 of catheter 1. As illustrated in FIGS. 2 through 12, the band-shaped electrode 51 may serve as a reference electrode for other electrodes on the catheter 1, whereby other voltages of other electrodes are determined relative to band-shaped electrode 51. In another embodiment of the invention, the band-shaped electrode serves as an ablation electrode and is provided with ablation energy to perform ablation. Reference is now made to FIG. 6, which illustrates a band-shaped ablation electrode 63. The band-shaped ablation electrode 63 may be provided with RF energy for ablation, and may be at least 4 mm in length to facilitate ablation. In a further embodiment of the invention, a band-shaped ablation electrode and a band-shaped temperature sensor are provided. Reference is now made to FIG. 7, which illustrates a band-shaped ablation electrode 65 and a band-shaped temperature sensor 67. Temperature sensor 67 may be a thermocouple, thermistor, or any other device for sensing temperature. The temperature sensor 67 detects the heat of the tissue during ablation by band-shaped ablation electrode 65. Temperature sensing is important during ablation because overheated tissue may explode or char, releasing debris into the bloodstream. Band-shaped ablation electrode 65 is connected to connector portion 7 via wire 66, which in turn connects to ablation energy generator 13; band-shaped temperature sensor 67 is connected to connector portion 7 via wire 68, which in turn connects to ablation controller 9. Band-shaped electrode 51 can serve as both a reference electrode and an ablation electrode, and may be switched between applications by the controller 9 or by a human operator.

Distal cap 57 has, up to this point, been described as being non-electrically conductive. In accordance with another aspect of the invention, distal cap 57 may be constructed of an electrically conductive material.

Figure 12:
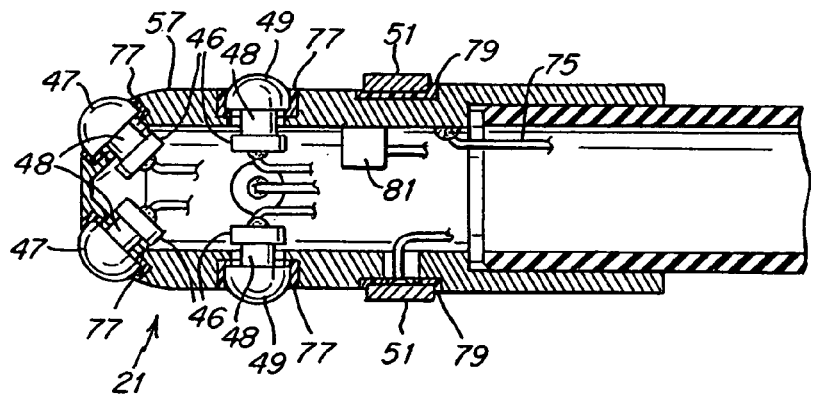
FIG. 12 illustrates a side cross-sectional view of the distal cap portion of a catheter in accordance with another embodiment of the present invention.
Figure 9:
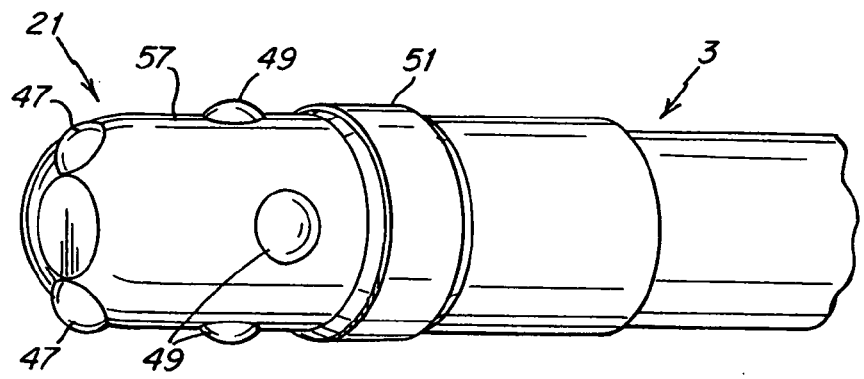
FIG. 9 illustrates a perspective view of the distal cap portion of a catheter in accordance with another embodiment of the present invention.

As illustrated in FIG. 12, distal cap 57 is disposed about mapping electrodes 47, 49 and band-shaped electrode 51. Distal cap 57 is connected via wire 75 to connector portion 7, which in turn connects to the ablation energy generator 13. Distal cap 57 may be formed of any suitable biocompatible, electrically conductive material (e.g., platinum, gold, titanium, iridium, stainless steel). To insulate mapping electrodes 47, 49 and band-shaped electrode 51 from conductive distal cap 57, insulating sleeves 77 and insulating sleeves 79 are respectively provided. Insulating sleeves 77 and insulating sleeves 79 may extend beyond mapping electrodes 47, 49 and band-shaped electrode 51 over the surface of distal cap 57 in a gasket-like formation. When RF ablation energy is delivered to conductive distal cap 57, as will be described below, RF energy may concentrate at the edges of the apertures distal cap 57. Insulation of the edge regions from tissue contact can prevent the delivery of excess ablation energy to the tissue from the edge regions of the distal cap 57.

Conductive distal cap 57 may be used to deliver ablation energy to a desired area of tissue. The ablation energy can be, for example, RF, DC, ultrasound, microwave, or laser radiation. Ablation may be performed in a blood vessel, e.g., the pulmonary vein, or an area of the heart, e.g., the left atrium. Ablation energy may be applied via the distal cap 57, to ablate the tissue that is in contact with the distal cap portion 21. For example, if an electrode on distal cap portion 21 detects an arrhythmia focus site in the vicinity of the electrode, the region of the distal cap 57 that is closest to the electrode may be used to ablate the tissue. Advantageously, repositioning of the catheter 1 is not necessary between detection of an arrhythmia focus site via a mapping electrode and ablation of the arrhythmia focus site via conductive distal cap 57. Further, because ablation can be confined to the particular region of interest, large areas of tissue need not be ablated, resulting in less extensive tissue scarring.

The embodiment illustrated in FIG. 12 has several advantages. The catheter is able to provide two functions, mapping and ablation, in a single catheter wherein the catheter is constructed and arranged to provide each of these functions individually and independently. The design of the catheter for high resolution mapping functions does not adversely impact the design for ablation functions. The catheter can be constructed so as to optimize each function. For example, the small size and location of each mapping electrode 49 on the distal cap portion 21 may be chosen to provide the ability to measure electrical activity with high resolution and an appropriate level of tissue contact, but without interference from either adjacent electrodes or other tissue not of interest. For ablation procedures, it is desirable to have a larger thermal mass to be able to apply more energy to the tissue and it is also desirable to have a larger surface area to transfer the energy to the tissue without overheating. Conductive distal cap 57 is able to meet these requirements since its surface area and mass are significantly larger than the mapping electrodes 49. Incorporating the small mapping electrodes 49 into apertures in the larger conductive distal cap 57 allows mapping and ablation procedures to be performed with a single catheter. In addition, since the mapping electrodes and the conductive distal cap can be operated independently, mapping and ablation procedures can be performed at the same time or in any desired sequence, such as before, during, and/or after each other.

Steering

Catheter 1 may be a steerable device. Reference is again made to FIG. 1, for description of one possible implementation for a steering mechanism for catheter 1. Catheter 1 is connected to catheter handle 5, which enables steering control of the distal end of catheter 1. In one embodiment of the invention, a control switch 23 is mechanically coupled to a steering wire 25, which is in turn mechanically coupled to the distal cap portion 21 of the catheter 1. As shown in FIG. 6, an anchor 59 may be provided in the distal cap portion 21 to fix the steering wire 25 to the inside of the catheter 1. The tension on the steering wire 25 may be adjusted by the control switch 23 to adjust a flexible portion of the distal end of the catheter 1. In particular, the control switch 23 may be maneuvered laterally along the control handle 5 to control the curvature of the distal end of the catheter 1. For example, the control switch 23 may be slid towards the proximal end of catheter 1 to move the distal end of the catheter 1 to position 27, and towards the distal end of control handle 5 to move the distal end of the catheter 1 to position 29. The control switch 23 may be slid to a position midway between the forward and backwards positions to orient the distal end of the catheter 1 in an uncurved position.

It should be appreciated that, although steering in a single plane is illustrated in FIG. 1, the catheter may be steered in any number of directions, in one or more planes. Further, although mechanical control of the steering wire 25 by control switch 23 is illustrated, control may be implemented electrically such that motion of a control switch 23 along the length of the control handle 5 is not required. Control may be implemented on the control handle 5, or via a device external to the catheter assembly. U.S. Pat. Nos. 5,383,852, 5,462,527, and 5,611,777, which are hereby incorporated by reference, illustrate various additional embodiments and features of control handle 5 that may be used for steering catheter 1.

Localization

Localization refers to a number of techniques whereby the location of catheter 1 in a patient can be determined. Apparatus and methods for localization can be incorporated into catheter 1.

Figure 8:
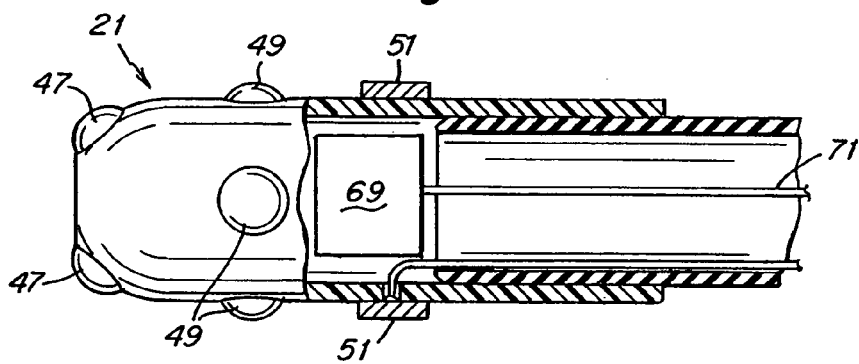
FIG. 8 illustrates a partial cross-sectional side view of the distal cap portion of a catheter in accordance with another embodiment of the present invention.

Reference is now made to FIG. 8, which illustrates a cross-sectional view of the distal cap portion 21 of catheter 1 including an electromagnetic sensor 69 that may be used for localization. Electromagnetic sensor 69, may be fixed within the shaft of the catheter 1 using any suitable mechanism, such as glue or solder. The electromagnetic sensor 69 generates signals indicative of the location of the electromagnetic sensor. A wire 71 electrically connects the electromagnetic sensor 69 to the controller 9, allowing the generated signals to be transmitted to the controller 9 for processing.

In addition to the electromagnetic sensor 69 fixed to the catheter, a second electromagnetic sensor (not shown) is provided that is fixed relative to the patient. The second electromagnetic sensor is attached, for example, to the patient's body, and serves as a reference sensor. A magnetic field is also provided, which is exposed to the electromagnetic sensors. Coils within each electromagnetic sensor generate electrical currents when exposed to the magnetic field. The electrical current generated by the coils of each sensor corresponds to a position of each sensor within the magnetic field. Signals generated by the reference electromagnetic sensor and electromagnetic sensor 69 fixed to the catheter are analyzed by the controller 9 to ascertain a precise location of electromagnetic sensor 69 fixed to the catheter 1.

Further, the signals can be used to generate a contour map of the heart. The map may be generated by contacting the catheter 1 with the heart tissue at a number of locations along the heart wall. At each location, the electric signals generated by the electromagnetic sensors are transmitted to the controller 9, or to another processor, to determine and record a location of the catheter 1. The contour map is generated by compiling the location information for each point of contact. This map may be correlated with heart signal data, measured by one or more electrodes on the catheter, for each location to generate a map of both the shape and electrical activity of the heart. Signals generated by the electromagnetic sensors may also be analyzed to determine a displacement of the catheter 1 caused by heartbeat.

As an alternative to the use of electromagnetic sensors other conventional techniques, such as ultrasound or magnetic resonance imaging (MRI) can also be used for localization of catheter 1.

In addition, an impedance-based sensor can also be incorporated into catheter 1. In an impedance-based system, several, such as three, high frequency signals are generated along different axes. The catheter electrodes may be used to sense these frequencies, and with appropriate filtering, the strength of the signal and thus the position of the catheter can be determined.

One skilled in the art will appreciate that the construction of catheter 1 may be optimized to make use of the various localization techniques.

Irrigation

Irrigation refers to any one of a number of techniques whereby a fluid may be introduced into the vicinity surrounding distal cap 21. Apparatus and methods for irrigation can be incorporated into catheter 1. The fluid may be a contrast fluid, a cooling fluid (particularly during ablation procedures), an antithrombogenic fluid, or other medicine. To introduce the fluid, a lumen may be provided inside shaft portion 3 that transports the irrigation fluid from the proximal end of catheter 1 to distal cap 21. The irrigation fluid may be dispersed into the vicinity surrounding distal cap 21 through apertures provided in the distal cap itself and/or through apertures in catheter shaft portion 3 proximal to distal cap 21. Alternatively, one or more of the electrodes in distal cap 49, such as electrodes 49, may be removed and the irrigation fluid directed through the aperture so created. Alternatively, the irrigation fluid may be introduced into the vicinity surrounding distal cap 21 by apertures in, for example, insulating sleeves 77.

Temperature Sensing

Temperature sensing refers to a number of techniques whereby the temperature in the vicinity surrounding distal cap 21 may be measured. Measuring temperature is important, particularly during ablation procedures, so as to avoid overheating or charring tissue. The catheter of the present invention can provide for measuring the temperature of the distal cap 21 and the mapping electrodes at the same time. The temperature of the distal cap can then be used to provide feedback for control of ablation energy generator 13 and the temperature of the mapping electrodes can be monitored to be certain that the tissue that is being ablated is in fact being destroyed or rendered non-electrically conductive.

A temperature sensor or sensors, such as, but not limited to one or more thermocouples 81 (illustrated in FIG. 9) may be attached to the catheter 1 for temperature sensing during ablation procedures. A temperature sensor may be in contact with the heart tissue (e.g., temperature sensor 67 of FIG. 7) or, alternatively, may not be in contact with the heart tissue (e.g., temperature sensor 81 of FIG. 9). In another embodiment, temperature sensors may be disposed within mapping electrodes 47, 49, 51, for example in a hole drilled within the electrode. One skilled in the art will appreciate that more than one temperature sensor may be used in any particular configuration of catheter 1.

Methods of Use

As discussed above, the catheter system of the invention may be used in mapping and/or ablation applications. In one embodiment of the invention, the mapping or ablation is performed in the heart of a patient. In the mapping application, multiple signals may be received from the heart tissue via multiple electrodes on the catheter. Each electrode may measure a continuous signal (i.e., electrogram) from the heart tissue. The continuous signal may represent the voltage of the heart tissue in contact with the electrode, with respect to a reference voltage, as it changes with time. The reference voltage may be obtained using a dedicated reference electrode or another measurement electrode. The quality of the signal received by each electrode improves as both the size of the electrode and the isolation of the electrode increases.

Preferably, multiple electrodes are employed, such that multiple electrograms may be obtained simultaneously. This allows for multiple data points, which can result in a more precise mapping of the heart signal and a shorter required measurement time. A shorter measurement time advantageously reduces the x-ray exposure to patients and physicians during fluoroscopy, when employed during the catheter procedure.

The mapping function of the catheter has a number of different applications. In one application, the catheter is used to measure the conductivity at various points of the septal wall, which separates the left and right sides of the heart, to determine a preferred sight for puncture of the septal wall. In another application, the conductivity of the heart tissue is measured between adjacent electrodes in contact with the heart tissue to determine the continuity of a lesion formed by ablation. In still another application, the catheter is used to identify electrical signals within the heart that are characteristic of a number of heart conditions. For example, the focus site of an arrhythmia (e.g., atrial fibrillation, AV nodal tachycardia or tachycardia resulting from Wolff-Parkinson-White syndrome). The mapping applications described above will be described in more detail in connection with various electrode configurations described below.

The signals measured by the electrodes of the catheter may be analyzed by the controller 9. In one embodiment, this analysis may take place in real time. In an alternate embodiment, these signals may be stored in recording device 17 for later analysis. These signals may be processed manually, via a human operator, or may be processed by controller 9 in connection with a processing algorithm. The processing algorithm may compare, add, subtract, or otherwise manipulate measured signals.

As will be described, the catheter can also be used for ablation procedures.

Figure 13:
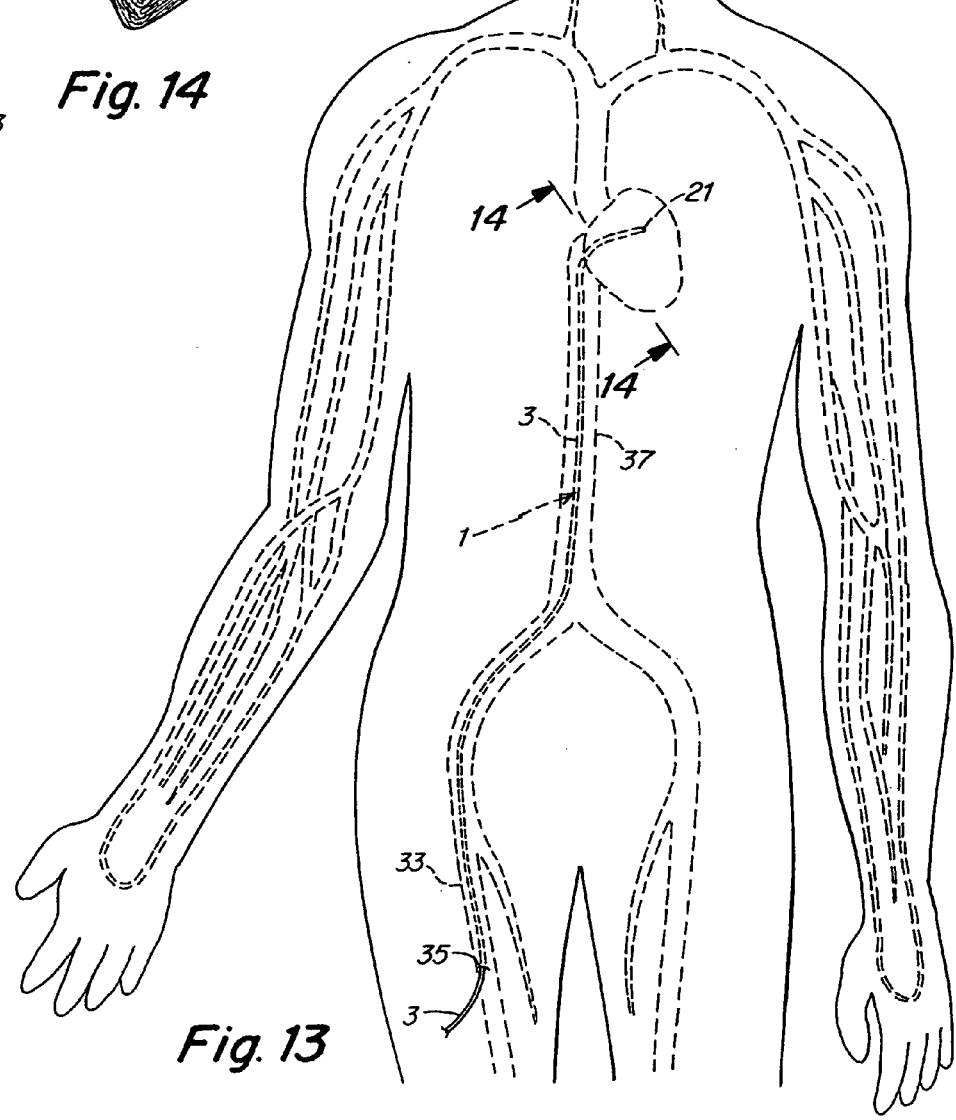
FIG. 13 illustrates insertion of the catheter of the present invention into a body.

Reference is now made to FIG. 13, which illustrates a method of insertion of the catheter 1 into a patient 31 in accordance with an embodiment of the present invention. The catheter 1 is inserted into the patient via a blood vessel, e.g., subclavian vein, jugular vein, or femoral vein. In FIG. 13, the catheter 1 is shown entering a femoral vein 33 via an incision 35 in the thigh of the patient 31. The catheter 1 may be introduced into the vein using a sheath/dilator (not shown). The sheath/dilator may be anchored at the incision site, for example by stitching the sheath/dilator to the patient's skin at the area of incision 35. From the incision site 35 in the femoral vein 33, the catheter 1 of FIG. 13 may be advanced independently, or through a sheath/dilator, up the inferior vena cava 37 into the right atrium of the heart.

Figure 14:
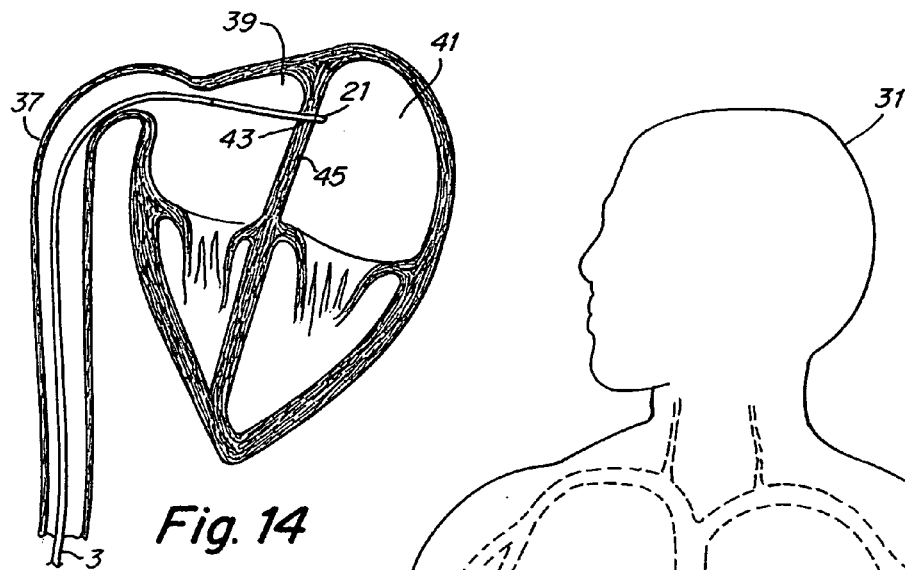
FIG. 14 illustrates the insertion of the catheter of the present invention into the heart.

Reference is now made to FIG. 14, which illustrates a diagram of a cross-sectional view of the heart taken along line A—A in FIG. 13. The catheter 1 is shown entering the right atrium 39 via the inferior vena cava 37. For passage of the catheter 1 into the left atrium 41, the catheter 1 may be passed trans-septally through the septal wall 45. In one method, a puncture 43 in the septal wall 45 is made at the foramen ovale, an area of the septal wall having a decreased thickness and decreased conductivity relative to other areas of the septal wall. As described previously, in one embodiment of the invention, electrodes on catheter 1 are used to locate the foramen ovale, or another preferred site to puncture the septal wall. As shown in FIG. 14, the catheter 1 traverses the septal wall 45 from the right atrium 39 and enters the left atrium 41. The catheter 1 may be used for mapping and/or ablation procedures in the left atrium 41 or may be maneuvered into the pulmonary vein(s) for mapping and/or ablation. It should be appreciated that the catheter may also be used to perform mapping and/or ablation in the right heart, in the ventricles, or in any other area of the heart or blood vessels of the circulatory system, and that the catheter 1 need not pass through the septal wall to enter these areas.

One advantage of using a catheter according to the invention in the described method is that only a single catheter is necessary to (1) determine the location of the foramen ovale for passage through the septal wall, (2) perform any desired mapping procedures, and (3) perform any desired ablation procedures. This avoids the need for changing catheters during procedures as between, for example, mapping and ablation procedures. It may also reduce the number of removal and reinsertion operations needed during a patient's electrophysiology study and treatment procedure.

The various configurations of the catheter illustrated in the figures are exemplary. One skilled in the art will appreciate that the number, size, orientation, and configuration of the mapping electrodes and the ablation electrodes, as well as various diameters and lengths of the catheter can be provided depending upon the particular application.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A method of determining a location for a septal wall puncture, comprising acts of:
providing a catheter with first and second electrodes on a distal tip of the catheter;
detecting a signal from each of the first and second electrodes;
determining, based on the signal from each of the first and second electrodes, an area of lowest conductivity on the septal wall; and
determining from the lowest conductivity a location for septal wall puncture.

* * * * *